United States Patent
Parikh et al.

(10) Patent No.: US 11,393,087 B2
(45) Date of Patent: Jul. 19, 2022

(54) OBJECTIVE ANALYSIS OF MEDICAL IMAGE DATA FOR WHITE MATTER ABNORMALITY

(71) Applicant: Children's Hospital Medical Center, Cincinnati, OH (US)

(72) Inventors: Nehal Parikh, Cincinnati, OH (US); Lili He, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 9 days.

(21) Appl. No.: 16/823,827

(22) Filed: Mar. 19, 2020

(65) Prior Publication Data

US 2020/0302602 A1 Sep. 24, 2020

Related U.S. Application Data

(60) Provisional application No. 62/875,137, filed on Jul. 17, 2019, provisional application No. 62/822,253, filed on Mar. 22, 2019.

(51) Int. Cl.
*G06T 7/00* (2017.01)
*G16H 30/40* (2018.01)

(52) U.S. Cl.
CPC .......... *G06T 7/0012* (2013.01); *G16H 30/40* (2018.01); *G06T 2207/10088* (2013.01); *G06T 2207/30016* (2013.01)

(58) Field of Classification Search
CPC . A61B 5/055; A61B 5/0042; A61B 2576/026; G06T 7/0012; G06T 7/11;

(Continued)

(56) References Cited

U.S. PATENT DOCUMENTS

2017/0344856 A1* 11/2017 Bonnier ................. A61B 5/055

OTHER PUBLICATIONS

He L et al., "Atlas-Guided Quantification of White Matter Signal Abnormalities on Term-Equivalent Age MRI in Very Preterm Infants: Findings Predict Language and Cognitive Development at Two Years of Age", PLoS ONE 8(12), 2013 (Year: 2013).*

(Continued)

*Primary Examiner* — Vu Le
*Assistant Examiner* — Julius Chai
(74) *Attorney, Agent, or Firm* — Frost Brown Todd LLC; Nicole M. Tepe

(57) ABSTRACT

A system for objectively analyzing medical image data for the presence of diffuse white matter abnormalities (DWMA) is configured to identify and determine DWMA characteristics that are not visually apparent. As compared to subjective visual diagnosis, objectively determined DWMA characteristics may be automatically compared to each other, and may be compared to and associated with various scales, evaluations, or other assessment criteria used to measure aspects of infant development. As a result, the disclosed system may objectively determine an impact that objectively determined DWMA characteristics will have on one or more developmental scales, which can be expressed as a time deficit, score deficit, or other value indicative of development deficits. The system may be integrated with medical imaging devices to provide near-immediate objective analysis for developmental impact at the point of care and in parallel with conventional imaging tasks, or may provide objective analysis results via a software interface.

14 Claims, 5 Drawing Sheets

(58) Field of Classification Search
CPC ........... G06T 2207/10088; G06T 2207/30016; G01R 33/56341; G01R 33/5608; G16H 30/40
See application file for complete search history.

(56) References Cited

OTHER PUBLICATIONS

He et al. "Automated detection of white matter singal abnormality using T2 relaxometry: Application to brain segmentation on term MRI in ver preterm infants", NeuroImage 64, p. 328-340, 2012. (Year: 2012).*
He et al. "Aberrant Executive and Frontoparietal Functional Connectivity in Very Preterm Infants with Diffuse White Matter Abnormalities", Pediatric Neurology, 53, p. 330-337, 2015. (Year: 2015).*
Parikh et al., "Automatically Quantified Diffuse Excessive High Signal Intensity on MRI Predicts Cognitive Development in Preterm Infants", Pediatric Neurology 49, p. 424-430, 2013. (Year: 2013).*
Altman, D.G., et al., "The cost of dichotomising continuous variables," BMJ, 2006, 332(7549):1080, 1 pg.
Amiel-Tison, C., et al., *Neurological Development from Birth to Six Years*, Baltimore, MD: The John Hopkins University Press, 2001, 2 pgs. (Publication information only.).
Anderson, P.J., et al., "Associations of newborn brain MRI with long-term neurodevelopmental impairments in very preterm children," J Pediatr, 2017, 187:58-65.e1, 18 pgs.
Anderson, R.I., et al., "The predictive validity of neonatal MRI for neurodevelopmental outcome in veiy preterm children," Semin Perinatol, 2015, 39:147-158, 12 pgs.
Ashburner. J., et al., "Unified segmentation." NeuroImage, 2005, 26(3):839-851, 13 pgs.
Baley, N., et al., *Bayley Scales of Infant and Toddler Development III*, Pearson, San Antonio, TX, 2005, 3 pgs. (Product Details Only.).
Beaino, G., et al., "Predictors of cerebral palsy in very preterm infants: the EPIPAGE prospective population-based cohort study," Dev Med Child Neurol, 2010, 52:e1 19-125, 7 pgs.
Benini, R., et al., "Normal Imaging in Patients with Cerebral Palsy: What Does It Tell US?" J Pediatr, 2013, 162:369-374.e1, 7 pgs.
Boardman, J.P., et al., "A common neonatal image phenotype predicts adverse neurodevelopmental outcome in children bom preterm," NeuroImage, 2010, 52(2):409-414, 6 pgs.
Brooks-Gunn, J., et al., "Early intervention in low-birth-weight premature infants. Results through age 5 years from the Infant Health and Development Program," JAMA, 1994, 272:1257-1262, 2 pgs. (Abstract only.).
Brostrom, L., et al., "Clinical Implications of Diffuse Excessive High Signal Intensity (DEHSI) on Neonatal MRI in School Age Children Born Extremely Preterm," PLoS One, 2016, 11(2):e0149578, 12 pgs.
Calloni, S.F., et al., "Neurodevelopmental outcome at 36 months in very low birth weight premature infants with MR diffuse excessive high signal intensity (DEHSI) of cerebral white matter," Radiol Med, 2015, 120(11):1056-1063, 8 pgs.
Campbell, M.J., et al., "Estimating sample sizes for binary, ordered categorical, and continuous outcomes in two group comparisons," BMJ, 1995, 311(7013): 1145-1148, 4 pgs.
Carlin, J.B., et al., "Regression models for twin studies: a critical review," Int J Epidemiol, 2005, 34(5): 1089-1099, 11 pgs.
Coggon, D., "Measurement error and bias," Chapter 4, In: BMJ, ed. *Epidemiology for the Uninitiated*. 4th ed.: BMJ Pub. Group, 1997, 7 pgs.
Counsell, S.J., et al., "Axial and Radial Diffusivity in Preterm Infants Who Have Diffuse White Matter Changes on Magnetic Resonance Imaging at Term-Equivalent Age," Pediatrics, 2006, 117(2):376-386, 11 pgs.
Damiano, D.L., "Activity, Activity, Activity: Rethinking Our Physical Therapy Approach to Cerebral Palsy," Phys Ther, 2006, 86(11): 1534-1540, 7 pgs.

De Bruine, F.T., et al., "Clinical Implications of MR Imaging Findings in the White Matter in Veiy Preterm Infants: a 2-year Follow-up Study," Radiology, 2011, 261(3):899-906, 8 pgs.
Dyet, L.E., et al., "Natural History of Brain Lesions in Extremely Preterm Infants Studied With Serial Magnetic Resonance Imaging From Birth and Neurodevelopmental Assessment," Pediatrics, 2006, 118(2):536-548, 13 pgs.
Ferriero, D.M., "Mri at term equivalent in preterm infants: the wise choice," Pediatr Res, 2018, 84(6):791-792, 2pgs.
Guillen, U., et al., "Relationship Between Attrition and Neurodevelopmental Impairment Rates in Extremely Preterm Infants at 18 to 24 Months: A Systematic Review," Arch Pediatr Adolesc Med, 2012, 166(2):178-184, 7 pgs.
Guyatt, G., et al., *Users' Guides to the Medical Literature: A Manual for Evidence-Based Clinical Practice*, 2nd ed., New York: McGraw-Hill Medical, 2008, 4 pgs. (Publication information only.).
Hadders-Algra, M., "Challenges and limitations in early intervention," Dev Med Child Neurol, 2011, 53(Suppl 4):52-55, 4pgs.
Hart, A., et al., "Neuro-developmental outcome at 18 months in premature infants with diffuse excessive high signal intensity on MR imaging of the brain," Pediatr Radiol, 2011, 41(10): 1284-1292, 9 pgs.
Hart, A.R., et al., "Appearances of diffuse excessive high signal intensity (DEHSI) on MR imaging following preterm birth," Pediatr Radiol, 2010, 40(8): 1390-1396, 7 pgs.
He, L., et al., "Optimization of magnetization-prepared rapid gradient echo (MP-RAGE) sequence for neonatal brain MRI," Pediatr Radiol, 2018, 48(8): 1139-1151, 27 pgs.
Herskind, A., et al., "Early identification and intervention in cerebral palsy," Dev Med Child Neurol, 2015, 57:29-36, 8 pgs.
Hintz, S.R., et al., "Neuroimaging and Neurodevelopmental Outcome in Extremely Preterm Infants," Pediatrics, 2015, 135(l):e32-e42, 11 pgs.
Honeycutt, A. A., et al., "Economic Costs of Mental Retardation, Cerebral Palsy, Hearing Loss, and Vision Impairment," In: Altman BM, Bamartt SN, Hendershot GE, Larson SA, eds. *Using Survey Data to Study Disability: Results From the National Health Interview Survey on Disability*. London, England: Emerald Group Publishing Limited, 2003:207-228, 7 pgs. (Abstract only.).
Ibrahim, J., et al., "Brain imaging in preterm infants <32 weeks gestation: a clinical review and algorithm for the use of cranial ultrasound and qualitative brain MRI," Pediatr Res, 2018, 84(6):799-806, 8 pgs.
Iwata, S., et al., "Qualitative Brain MRI at Term and Cognitive Outcomes at 9 Years After Very Preterm Birth," Pediatrics, 2012, 129(5):e1138-e1147, 10 pgs.
Jeon, T.Y., et al., "Neurodevelopmental Outcomes in Preterm Infants: Comparison of Infants with and without Diffuse Excessive High Signal Intensity on MR Images at Near-term-equivalent Age," Radiology, 2012, 263(2):518-526, 9 pgs.
Johnston, M.V., "Plasticity in the Developing Brain: Implications for Rehabilitation," Dev Disabil Res Rev, 2009, 15:94-101, 8 pgs.
Kidokoro, H., et al., "High Signal Intensity on T2-Weighted MR Imaging at Term-Equivalent Age in Pretenn Infants Does Not Predict 2-Year Neurodevelopmental Outcomes," AJNR Am J Neuroradiol, 2011, 32(11):2005-2010, 6 pgs.
Kidokoro, H., et al., "New MR Imaging Assessment Tool to Define Brain Abnormalities in Veiy Preterm Infants at Term," AJNR Am J Neuroradiol, 2013, 34(11):2208-2214, 7 pgs.
Krishnan, M.L., et al., "Relationship Between White Matter Apparent Diffusion Coefficients in Preterm Infants at Term-Equivalent Age and Developmental Outcome at 2 Years," Pediatrics, 2007, 120(3):e604-e609, 6 pgs.
Kuban, K.C., et al., "Girls and Boys Born before 28 Weeks Gestation: Risks of Cognitive, Behavioral, and Neurologic Outcomes at Age 10 Years," J Pediatr, 2016, 173:69-75.e1, 8 pgs.
Landis, J.R., et al., "The Measurement of Observer Agreement for Categorical Data," Biometrics, 1977, 33(1):159-174, 16 pgs.
Larroque, B., et al., "Neurodevelopmental disabilities and special care of 5-year-old children born before 33 weeks of gestation (the EPIPAGE study): a longitudinal cohort study," Lancet, 2008, 371(9615):813-820, 8 pgs.

(56) References Cited

OTHER PUBLICATIONS

Maalouf, E.F., et al., "Magnetic resonance imaging of the brain in a cohort of extremely preterm infants," J Pediatr, 1999, 135(3):351-357, 7 pgs.

Molinaro, A.M., et al., "Prediction error estimation: a comparison of resampling methods," Bioinformatics, 2005, 21(15):3301-3307, 7 pgs.

Morel, B., et al., "Neonatal brain MRI: how reliable is the radiologist's eye?" Neuroradiology, 2016, 58(2): 189-193, 5 pgs.

Morgan, C., et al., "Single blind randomised controlled trial of GAME (Goals—Activity—Motor Enrichment) in infants at high risk of cerebral palsy," Res Dev Disabil, 2016, 55:256-267, 12 pgs.

Murner-Lavanchy, I.M., et al., "Thirteen-Year Outcomes in Very Preterm Children Associated with Diffuse Excessive High Signal Intensity on Neonatal Magnetic Resonance Imaging," J Pediatr, 2019, 206:66-71.e1, 7 pgs.

Nongena, P., et al., "Confidence in the prediction of neurodevelopmental outcome by cranial ultrasound and MRI in preterm infants," Arch Dis Child Fetal Neonatal Ed, 2010, 95(6):F388-F390, 3 pgs.

Novak, L, et al., "Early, Accurate Diagnosis and Early Intervention in Cerebral Palsy Advances in Diagnosis and Treatment," JAMA Pediatr, 2017, 171(9):897-907, 11 pgs.

Palisano, R., et al., "Development and reliability of a system to classify gross motor function in children with cerebral palsy," Dev Med Child Neurol, 1997, 39:214-223, 10 pgs.

Parikh, N.A., "Advanced neuroimaging and its role in predicting neurodevelopmental outcomes in very preterm infants," Semin Perinatol, 2016, 40(8):530-541, 21 pgs.

Parikh, N.A., et al., "Early Detection of Cerebral Palsy Using Sensorimotor Tract Biomarkers in Very Preterm Infants," Pediatr Neurol, 2019, 98:53-60, 18 pgs.

Parikh, N.A., et al., "Neuropathology Associated With Diffuse Excessive High Signal Intensity Abnormalities on Magnetic Resonance Imaging in Very Preterm Infants," Pediatr Neurol, 2016, 65:78-85, 8 pgs.

Parikh, N.A., et al., "Perinatal Factors and Regional Brain Volume Abnormalities at Term in a Cohort of Extremely Low Birth Weight Infants," PLoS One, 2013, 8(5):e62804, 11 pgs.

Pierson, C.R., et al., "Gray matter injury associated with periventricular leukomalacia in the premature infant," Acta Neuropathol, 2007, 114(6):619-631, 13 pgs.

Pogribna, U., et al., "Perinatal Clinical Antecedents of White Matter Microstructural Abnormalities on Diffusion Tensor Imaging in Extremely Preterm Infants," PLoS One, 2013, 8(8):e72974, 7 pgs.

Sellier, E., et al., "Decreasing prevalence in cerebral palsy: a multi-site European population-based study, 1980 to 2003," Dev Med Child Neurol, 2016, 58:85-92, 8 pgs.

Shepherd, R., ed., *Cerebral Palsy in Infancy: Targeted Activity to Optimize Early Growth and Development*, 1st ed: Elsevier Ltd., 2013, 8 pgs. (Table of Contents Only.).

Shevell, M., "Cerebral palsy to cerebral palsy spectram disorder: Time for a name change?" Neurology, 2019, 92:233-235, 3 pgs.

Shi, F., et al., "Infant Brain Atlases from Neonates to 1- and 2-Year-Olds," PLoS One, 2011, 6(4):e18746, 11 pgs.

Skiold, B., et al., "Neonatal Magnetic Resonance Imaging and Outcome at Age 30 Months in Extremely Preterm Infants," J Pediatr, 2012, 160(4):559-566.e1, 9 pgs.

Skiold, B., et al., "White matter changes in extremely preterm infants, a population-based diffusion tensor imaging study," Acta Paediatr, 2010, 99(6):842-849, 8 pgs.

Slaughter, L.A., et al., "Early Conventional MRI for Prediction of Neurodevelopmental Impairment in Extremely Low Birth Weight Infants," Neonatology, 2016, 110(1):47-54, 16pgs.

Spittle, A., et al., "Early developmental intervention programmes provided post hospital discharge to prevent motor and cognitive impairment in preterm infants (Review)," Cochrane Database Syst Rev, 2015, Issue 11, Art. No. CD005495, 87 pgs.

Springer, A., et al., "Profile of children with cerebral palsy spectrum disorder and a normal MRI study," Neurology, 2019, 93:e88-e96, 9 pgs.

Teli, R., et al., "Postnatal Microstructural Developmental Trajectory of Corpus Callosum Subregions and Relationship to Clinical Factors in Very Preterm Infants," Sci Rep, 2018, 8(1):7550, 12 pgs.

Van Hus, J.W., et al., "Motor impairment in very preterm-born children: links with other developmental deficits at 5 years of age," Dev Med Child Neurol, 2014, 56:587-594, 8 pgs.

Van't Hooft, J., et al., "Predicting developmental outcomes in premature infants by term equivalent MRI: systematic review and meta-analysis," Syst Rev, 2015, 4:71, 10 pgs.

Volpe, J.J., "Confusions in Nomenclature: "Periventricular Leukomalacia" and "White Matter Injury"-Identical, Distinct, or Overlapping?" Pediatr Neurol, 2017, 73:3-6, 4 pgs.

Williams, J., et al., "Prevalence of motor-skill impairment in preterm children who do not develop cerebral palsy: a systematic review," Dev Med Child Neurol, 2010, 52:232-237, 6 pgs.

Wisnowski, J.L., et al., "Altered Glutamatergic Metabolism Associated with Punctate White Matter Lesions in Preterm Infants," PLoS One, 2013, 8(2):e56880, 8 pgs.

Wisnowski, J.L., et al., "Magnetic resonance spectroscopy markers of axons and astrogliosis in relation to specific features of white matter injury in preterm infants," Neuroradiology, 2014, 56(9):771-779, 9 pgs.

\* cited by examiner

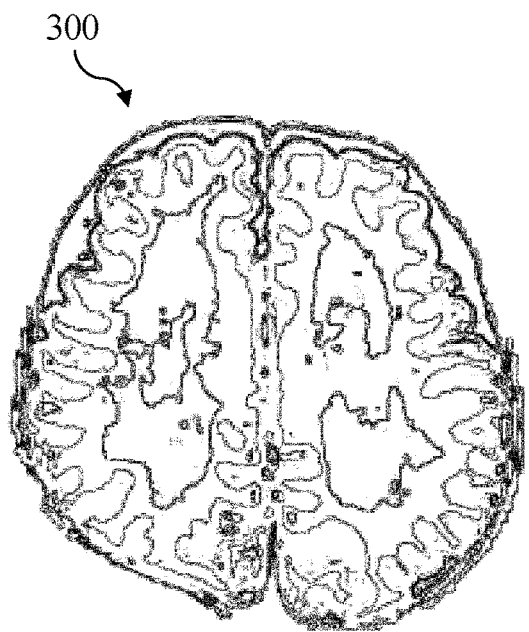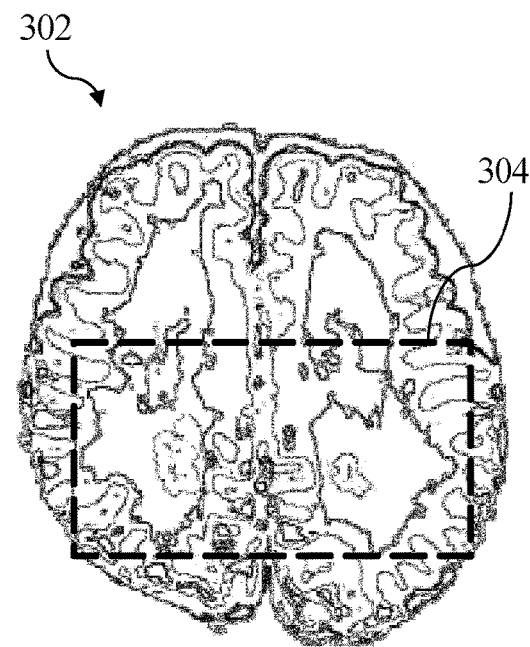
FIG. 7A  FIG. 7B
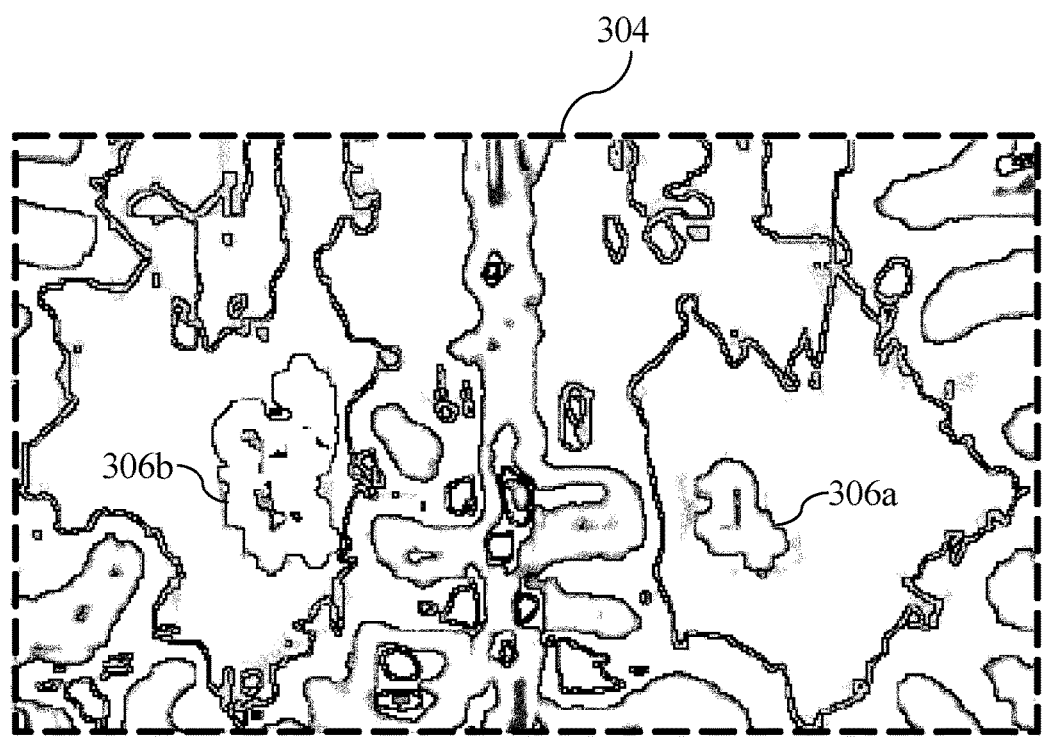
FIG. 7C

OBJECTIVE ANALYSIS OF MEDICAL IMAGE DATA FOR WHITE MATTER ABNORMALITY

PRIORITY

This application is a non-provisional claiming priority to U.S. Provisional Patent App. 62/875,137, filed Jul. 17, 2019 and titled "Novel Diffuse White Matter Abnormality Biomarker Predicts Motor Outcomes in Very Preterm Infants", and U.S. Provisional Patent App. 62/822,253, filed Mar. 22, 2019 and titled "Objectively-Quantified Diffuse White Matter Abnormality at Term is an Independent Predictor of Cognitive and Language Outcomes in Very Preterm Infants", the disclosures of each of which are hereby incorporated by reference in their entirety.

GOVERNMENT SUPPORT CLAUSE

This invention was made with government support under NS096037, HD094085 and NS094200awarded by the National Institutes of Health. The government has certain rights in the invention.

FIELD

The disclosed technology pertains to a system for performing an objective analysis of medical image data to predict neurological conditions.

BACKGROUND

Despite ongoing improvements in perinatal care, the prevalence of neurodevelopmental impairments (NDI) remains very high in groups such as very preterm infants (e.g., less than 32 weeks gestational age), with up to 40% of such groups experiencing long-term cognitive, language, motor, and behavioral abnormalities. Accurate diagnosis of such abnormalities can require five or more years of examination and observation. Without effective tools for early detection, interventional therapies and treatments cannot be precisely targeted to patients in need. Further, many parents of children with concerns about developmental deficits must wait for long periods of time with limited ability to confirm or rebut their concerns. As a result of limited resources and missed identification, many patients with such abnormalities go without treatment during periods of peak neuroplasticity during childhood.

Some screening techniques that may provide early detection have been attempted but have only shown minor improvements in the timeframe and accuracy of detection. One such example includes brain magnetic resonance imaging (MM) screening at term-equivalent age, in which trained experts may visually examine medical image data for a patient and provide an opinion on the likelihood of future abnormalities. However, such screening relies on visual qualitative diagnosis after examination of an MRI dataset, and as a result is of limited effectiveness due to the subtle pathology exhibited by preterm infants, including microstructural, metabolic, and maturational abnormalities that are not readily visible, or are not reliably represented in neonatal structural MRI datasets. The limitations of such screening can result in false positives and inefficient direction of limited treatment resources, and can also result in abnormalities remaining undiagnosed and untreated during the time in which the patient would most benefit.

What is needed, therefore, is an improved system for objective analysis of medical image data for white matter abnormalities.

BRIEF DESCRIPTION OF THE DRAWINGS

The drawings and detailed description that follow are intended to be merely illustrative and are not intended to limit the scope of the invention as contemplated by the inventors.

FIG. 7A shows an exemplary medical image;

FIG. 7B shows the medical image of FIG. 7B after objective analysis according to the steps of FIG. 2;

FIG. 7C shows a magnified portion of the medical image of 7B that includes objectively identified white matter abnormalities.

DETAILED DESCRIPTION

Figure 1:
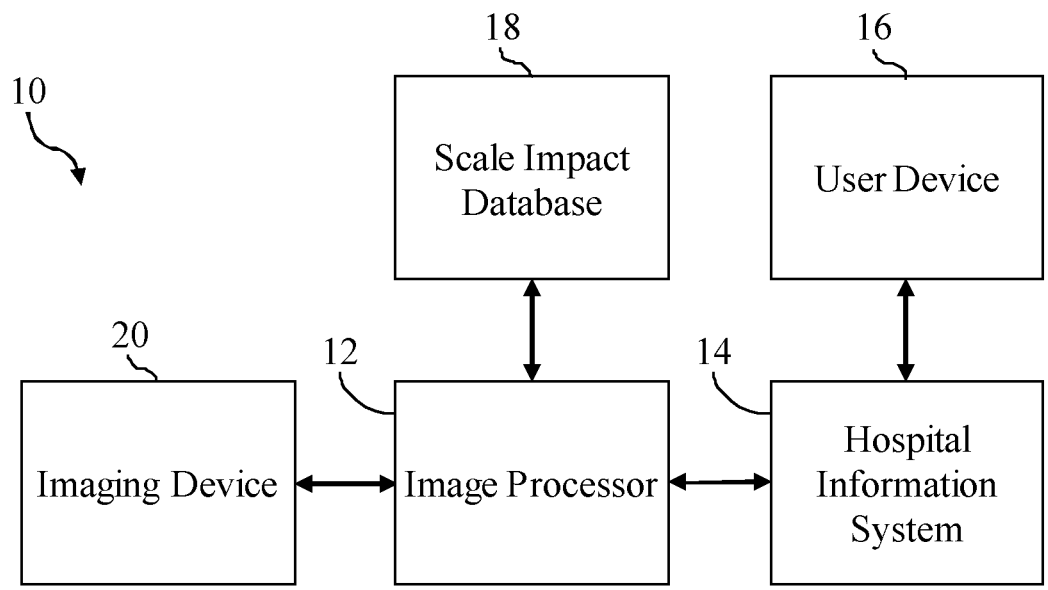
FIG. 1 is a schematic diagram of an exemplary system configured to perform objective analysis of medical image data for white matter abnormalities.

The inventors have conceived of novel technology that, for the purpose of illustration, is disclosed herein as applied in the context of a system for objective analysis of medical image data to predict neurological conditions. While the disclosed applications of the inventors' technology satisfy a long-felt but unmet need in the art of objective analysis of medical image data, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

I. Diffuse White Matter Abnormality and Development

Qualitative diagnosis is especially unreliable for predicting diffuse excessive high signal intensity (DEHSI), or diffuse white matter abnormality (DWMA), which is one of the most prevalent abnormalities and is observed in 50-80% of very preterm infants in some medical imaging and screening scenarios (e.g., term-equivalent age T2-weighted MRI). This imaging signal abnormality is believed to be either a delay in white matter maturation or subtle pathology, possibly on the milder end of the spectrum of periventricular leukomalacia. There are few identified risk factors associated with the development of DWMA, due at least in part to the unreliability of qualitative, subjective analysis and diagnosis. Conversely, quantitative, or objective analysis associated with DWMA suggests a relationship between metabolite abnormalities, axonopathy, and myelinopathy in regions of DWMA.

The results of objective diagnosis of DWMA also suggest a strong association between DWMA and various development factors suggestive of a neurodevelopment impairment (NDI), including impact on standardized cognitive, language, and motor function evaluations. In contrast, subjective visual diagnosis of DWMA has frequently failed to identify any association between DWMA and NDI. Development of the disclosed technology included externally validating objectively diagnosed DWMA is an independent predictor of cognitive, language, and motor development in very preterm infants without severe structural injury. This predictor can be accurately used for early risk stratification and targeted enrollment in post-discharge early intervention therapies and neuroprotection trials.

External validation included analyses of approximately 80% of all very preterm infants born in the Columbus, Ohio region over a period of several years, excluding any infants with congenital or chromosomal anomalies that affected the central nervous system, infants that remained hospitalized at 44 weeks postmenstrual age (PMA), infants showing excessive motion artifacts, and To provide a comparison between objectively analyzed and visually analyzed DWMA, pediatric neuroradiologists performed all structural Mill readings using a standardized published scoring system for qualitative grading for severity of structural brain injury/maturation and the objective quantitative biometric measurements were all made separately by a single trained expert to produce a global brain abnormality score. Visual, qualitative assessment of DWMA was made by a single reader with greater than 10 years of experience in interpreting neonatal MRI scans and masked to all clinical and quantitative DWMA information.

Qualitative DWMA scoring was based on severity and extent where infants with no DWMA or high signal intensity only in the periventricular crossroads were graded as 0, while grade 1 was assigned if DMWA only visible in one region, grade 2 was assigned if DWMA was visible in two regions, and grade 3 was assigned if three or more regions were involved in addition to the normal signal intensity observed in the crossroads. The reader also assessed whether the margins of the posterior crossroads were visible. Intra-rater agreement on the DWMA grade was assessed by using kappa ($\kappa$) statistic following reevaluation of randomly selected MRI scans by the same rater three weeks later. Of the reevaluated subjects, complete agreement was seen in 60.0% of cases (e.g., expected agreement 31.0%) for a K of 0.42, which represents a moderate strength of agreement.

Participating infants were evaluated at 2 years corrected age at a high-risk follow up clinic. Assessments included standardized cognitive and language development using the Bayley Scales of Infant and Toddler Development, Third Edition (e.g., Bayley-III). The composite scores for the two Bayley-III subscales (e.g., cognitive and language) are scaled to metric with a mean of 100, standard deviation of 15, and range from 40 to 160. A score that was 3 standard deviations below the normative mean was assigned to children that could not complete the test because it was too difficult.

The relationship between DWMA characteristics and Bayley cognitive and language scores at 2 years corrected age was determined by linear regression fitted using maximum likelihood estimation (MLE) to allow for correlations between twins in the study to be explicitly modeled. To evaluate the independent prognostic value of normalized volume of DWMA (e.g., DWMA volume divided by total white matter volume), multivariable regression models were performed by adding known perinatal predictors of Bayley scores, including socioeconomic status (e.g., maternal education, income, and insurance status), gestational age, sex and global brain abnormality score. In addition, location and PMA at the time of imaging was considered in both final models to exclude differences in clinical characteristics between hospital sites and age at MRI scan as significant factors.

In secondary analyses, Fisher's exact test was used to examine prognostic test properties and the association between objectively-diagnosed severe DWMA and visually-diagnosed severe DWMA and moderate injury on structural MM with cognitive deficits and language deficits. Objectively-diagnosed severe DWMA was defined as the normalized volume of DWMA>75th percentile, and was also tested at a higher threshold of >90th percentile. Traditional two-sided P value of <0.05 was used to indicate statistical significance.

For infants with high quality images suitable for DWMA quantification, 76% returned for neurodevelopmental testing. Infants that returned for follow-up were not significantly different from those that did not in their baseline characteristics. Additionally, the global brain abnormality scores and DWMA volumes were not significantly different between infants with and without follow-up. The Bayley-III mean cognitive and language scores at 24.2 months corrected age were 99.1 and 96.4, respectively. Structural MRI was performed at a mean PMA of 40.3 weeks. Based on the global brain abnormality score, 71.6% of infants were classified as having no injury, 21.6% with mild injury, and 6.8% with moderate injury exhibited by their structural MRI at term-equivalent age. Punctate white matter lesions were observed in 14.3% of infants and cerebellar hemorrhage in 5.1% of infants. Neither abnormality on its own or in combination was found to be predictive of Bayley cognitive or language scores at 2 years corrected age. Visual qualitatively defined DWMA was diagnosed as grade 3 in 13.5% of infants, grade 2 in 28.4% of infants, and grade 0 in 58.1% of infants. Only one infant was diagnosed with invisible posterior crossroads.

Normalized volume of DWMA was found to be a significant predictor of Bayley cognitive and language scores in bivariable analyses. This association remained significant even when raw DWMA volume was tested with tissue or total brain volumes in the regression analyses. In multivariable analyses, controlling for other known predictors of Bayley scores, including socioeconomic status (SES), gestational age, sex, and global brain abnormality score, normalized volume of DWMA remained a significant predictor of cognitive and language development at 2 years corrected age. An increase of 10% in DWMA volume and low SES were significantly predictive of a 15-point (e.g., 1.0 standard deviation) and 8-point reduction (e.g., 0.53 standard deviation) in Bayley-III cognitive scores, respectively. DWMA volume and low SES were also predictive of language scores, with a 10% increase in DWMA volume and low SES predictive of an approximate 8-point and 7-point decrease in language scores, respectively.

Non-normalized DWMA volume (e.g., DWMA volume not divided by total white matter volume) exhibited similar coefficients in predicting Bayley scores. Visual, qualitative diagnosis of DWMA was not significantly predictive of cognitive or language scores. Inclusion of known predictors/covariates in the model did not substantially change these relationships.

In secondary analyses, objectively-diagnosed moderate-severe DWMA (e.g., 75th percentile threshold) significantly predicted cognitive deficits but not language deficits. In post-hoc exploratory analyses, a 90th percentile threshold resulted in higher accuracy for cognitive and language deficits.

Objectively-diagnosed severe DWMA (e.g., >90th percentile) predicted cognitive deficits at age 2 with 100.0% sensitivity and 95.7% specificity. In comparison, moderate injury on structural MM exhibited lower predictive value for cognitive deficits and visually-diagnosed severe DWMA (e.g., grade 3) did not significantly predict cognitive or language deficits. Combining visually-diagnosed, moderate-severe grades of DWMA (e.g., grade 2) did not improve prediction of cognitive or language deficits.

Based on the above, it is apparent that objectively measuring DWMA volume is predictive of lower cognitive and language scores at 2 years corrected age in very preterm infants without severe injury. Additionally, there is no apparent significant association between visual, qualitative diagnosis of DWMA and Bayley-III scores. Thus, objective analysis advantageously allows for improved accuracy in early counseling and treatment related to developmental risks, as well as targeted and aggressive early intervention therapies and novel neuroprotective interventions. As an example, a very preterm infant that has objectively analyzed severe DWMA would have a 94% post-test probability of developing cognitive deficit at 2 years of age, while infants with less than severe or moderate-severe DWMA would not be at risk for cognitive deficit. Thus, limited resources that are available for treatment and intervention may be targeted at a subset of infants rather than more generally provided to all preterm infants.

A number of factors have historically prevented DWMA characteristics from being utilized in developmental predictions based upon subjective visual analysis. First, the common presence of signal inhomogeneity and normal occurrence of developmental crossroads on term equivalent age MRI can readily confound DWMA diagnosis and reduce diagnostic reliability. This lower reliability can significantly increase measurement error, thereby reducing the likelihood of finding a significant association even where one truly exists. Second, even when qualitative DWMA diagnostic reliability is satisfactory, there is no gold standard test to confirm DWMA diagnosis. As a result, what is being subjectively labeled as DWMA may not be true pathology. Lastly, a qualitative visual diagnosis will inherently have lower study power than a quantitative diagnosis (e.g., categorical vs. continuous variable) to find an association, thus reducing confidence in any associations that are identified for a given sample size, especially when the sample size is small.

The above disclosed developments suggest that DWMA on MRI is likely more akin to the diffuse white matter gliosis without focal necrosis reported from postmortem brain tissue studies. If axonal loss is a predominant feature of DWMA, then the reduction in functional connectivity of important cognitive and attention networks may explain the lower cognitive scores in infants with objectively-diagnosed DWMA. The common occurrence of DWMA in the centrum semiovale, a central white matter region that contains several association, projection, and commissural fibers, may also explain its association with cognitive deficits. Any inflammatory (e.g. sepsis, bronchopulmonary dysplasia) or hypoxic-ischemic insult to this region is likely to adversely impact myelination and/or axonal development of more structural brain networks than insults in peripheral subcortical white matter regions, and consequently result in more functional consequences.

Additional supportive evidence of the neuropathological nature of DWMA comes from studies that have identified several perinatal/neonatal risk factors for DWMA, including ligation surgery for patent ductus arteriosus, retinopathy of prematurity, necrotizing enterocolitis, and prolonged mechanical ventilation/bronchopulmonary dysplasia. Typically, these illnesses precede the natural time course of DWMA development, as DWMA has not been reported much earlier than 36 weeks PMA or after 50 weeks PMA. The peak prevalence of DWMA is around term-equivalent age. The significant association of DWMA with such antecedent risk factors and NDI suggests that DWMA lies intermediate on the pathway between some of these prevalent neonatal illnesses and NDI.

These various findings support the use of DWMA as an objective intermediate biomarker to assess the effects of neonatal neuroprotective interventions that are targeted at reducing the burden of DWMA and consequently long-term cognitive impairments. In addition, ongoing objective analysis of DWMA will produce datasets that may accelerate the conduct and efficiency of phase I and II trials of neuroprotective agents. As compared to the current approach of evaluating all very preterm infants for delays/deficits, objective analysis could accurately stratify risk and permit targeted, aggressive early intervention therapies and the design of new therapies for such higher risk infants while avoiding unnecessary therapies and harms from new treatments for infants identified at low risk.

II. Objective Analysis of DWMA for Language and Cognitive Function

As has been described, objective analysis of DWMA can provide valuable opportunities to improve current approaches to preterm infants. Some advantageous implementations of the disclosed objective analysis techniques will include a system configured to automatically quantify and report DWMA characteristics and any associated patient impacts (e.g., developmental deficits). Some implementations may be readily connected to or integrated with clinical MRI platforms or other imaging device, and may be configured to provide near-immediate results (e.g., within several minutes of receipt of medical image data). In some implementations, this may allow for the information to be rapidly available at the point of care, following MRI acquisition or as part of other standard processes associated with preterm infants. In other implementations, such information may be rapidly available from a remote source (e.g., a cloud-based image processor accessible via software interface) once transmitted from a hospital information system or another device where they are stored. In these examples and others, the objective analysis may be performed without significant additional processes or equipment, and so may be introduced or retrofitted into many existing neonatal technology and process frameworks without significant cost.

Turning now to the figures, FIG. 1 shows a schematic diagram of an exemplary system (10) configured to perform objective analysis of medical image data for white matter abnormalities. The system (10) includes an imaging device (20) that is usable to capture or produce medical image data, and may include, for example, a magnetic resonance imaging (MM) machine, a computed tomography (CT) scanner, or another medical imaging device. An image processor (12) is configured to receive and modify or otherwise process medical image data captured by the imaging device (20) into various forms that may be used for objective analyses of DWMA. The image processor (12) will vary by implementation, but may include one or processors and memories, and may be a component of the imaging device (20) or may be configured as one or more physical servers, virtual servers, cloud servers or other cloud computing environments, for example.

A hospital information system or "HIS" (14), which may include one or more servers or other computing devices, is in communication with the image processor (12), and is configured to receive, store, and provide various information related to operation of the system (10). Information exchanged with the HIS (14) may include, for example, patient medical records (e.g., basic patient data, physiological information, demographics and other background information), equipment records (e.g., model information and maintenance information for the imaging device (20)), staff records (e.g., identities and credentials for users of the imaging device (20)), and other information.

A scale impact database (18) is accessible by the image processor (12) and may include one or more databases, data sets, data storages, or other data sources. The scale impact database (18) is configured to store information related to one or more infant developmental scales, assessments, evaluations, or other datasets, and may also store information describing associations between infant physiological factors, demographics, medical conditions, or other aggregate data and infant development.

A user device (16) is in communication with the HIS (14), and may include a computer, smartphone, tablet, medical device, or other computing device that is capable of exchanging information with the HIS (14). Exchanged information may include, for example, notifications describing results of analyses or patient treatment plans, results of patient treatment or evaluation, or other information related to the long-term presentation of developmental issues by patients, or the evaluation and treatment of such developmental issues. It should be understood that the system (10) is exemplary, and that varying implementations of systems capable of objective analyses of medical image data exist and are suitable. As an example, some implementations of such a system may only include the imaging device (20) and image processor (12), while other implementations my only include the image processor (12) and may receive medical image data from various external sources. Further, some implementations of such a system may include additional devices not shown in FIG. 1, or interconnected within a communication network in ways other than shown in FIG. 1, with such variations being apparent to those of ordinary skill in the art in light of this disclosure.

Figure 2:
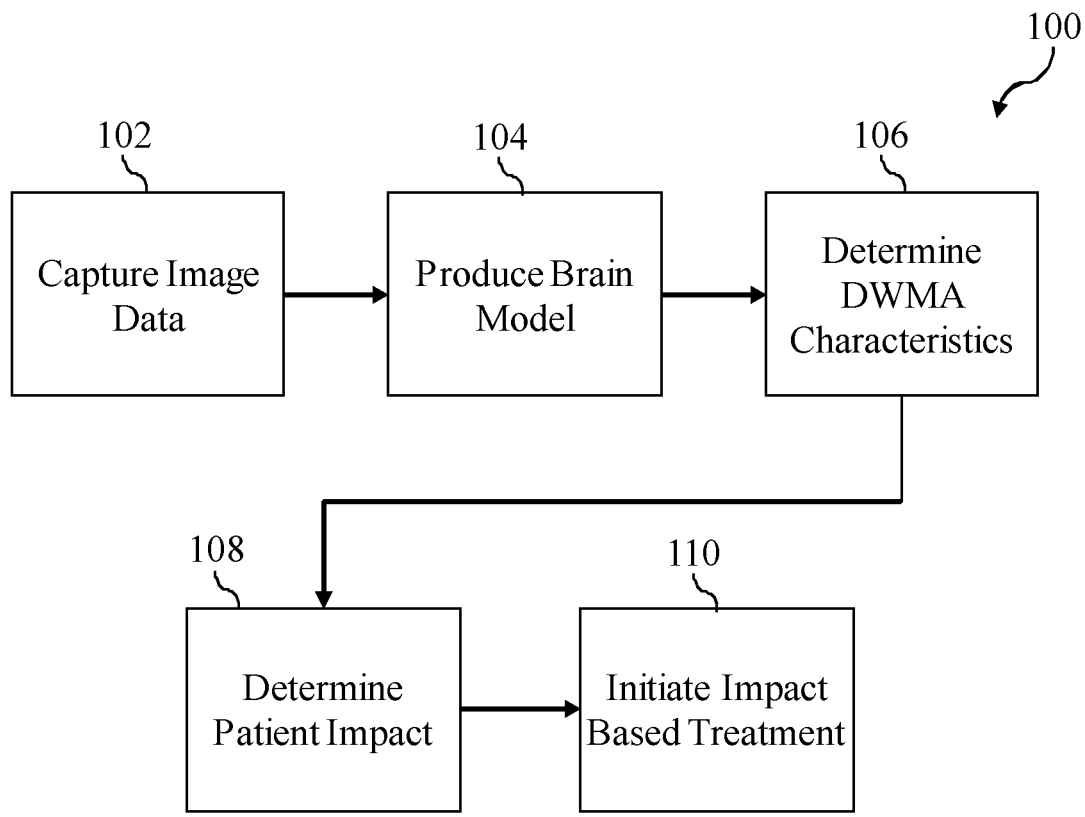
FIG. 2 is a flowchart of an exemplary set of high-level steps that could be performed with the system of FIG. 1 to objectively analyze medical image data.

FIG. 2 is a flowchart of an exemplary set of high-level steps (100) that could be performed with the system of FIG. 1 to objectively analyze medical image data. FIGS. 3-6 each show more detailed steps that may be performed during the high-level steps (100) of FIG. 2, and will be discussed in further detail below. Image data may be obtained in varying ways, which may include capturing (102) the image data with a device such as the imaging device (20), but may also include receiving the image data from another device via a software interface, a network connection, or a portable storage device. For example, in an implementation where the image processor (12) is part of the imaging device (20), the image data may be available to the image processor (12) immediately upon being captured (102) by the imaging device (20) (e.g., upon the completion of an MRI scan). As another example, in an implementation where the image processor (12) is a remotely located server or cloud computing environment, image data may be captured (102) by the imaging device (20) and then transmitted to the image processor (12) at a later time via a software interface or other communication channel (e.g., such as web-based API that receives image data and returns modified image data and/or other results of objective analysis).

When capturing (102) medical image data with an MRI, some conditions and configurations may be advantageous in improving image accuracy and reducing artifacts, including: capture of structural MRI on an MRI scanner (e.g., 3T Siemens Skyra) and 32-channel phased array head coil; image data captured during infant's initial hospitalization in the NICU; image data captured between 39 and 44 weeks post menstrual age (PMA); and image data captured during natural sleep and without sedation by feeding infants immediately prior to the scan, providing hearing protection and using an immobilization device. Advantageous configurations include: axial T2-weighted: echo time 147, repetition time 9500 ms, flip angle 150°, resolution 0.93×0.93×1.0 mm$^3$, scan time 4:09 min.; 3D MPRAGE: echo time 2.9, repetition time 2270 ms, echo spacing time 8.5 ms, flip angle 13°, resolution 1.0×1.0×1.0 mm$^3$, time 3:32 min.; and axial SWI: echo time 20, repetition time 27 ms, flip angle 15°, resolution 0.7×0.7×1.6 mm$^3$, time 3:11 min.

After medical image data is captured or otherwise received, the image processor (12) may produce (104) a brain model from the medical image data. The medical image data may be received in a form that can be converted into or interpreted as a set of image slices that, in sequence, represent the patient's brain when viewed in layers from one or more directions or perspectives (e.g., sagittal, axial, coronal). Producing (104) a model from the medical image data may include, for example, selecting one or more image slices for inclusion in the model, filtering one or more image slices from the model, segmenting one or more image slices into voxels, segment one or more image slices in order to identify discrete anatomy, or other image processing actions. Producing (104) the model may also include associating additional characteristics with parts of the model, such as associating various characteristics with voxels or other segmented anatomy (e.g., identifying a portion of the model as a particular anatomical structure, identifying a voxel within the model as being associated with a particular type of tissue, density, or other property).

Once prepared, a brain model may then be analyzed to determine (106) one or more characteristics associated with DWMA. Such DWMA characteristics may include identification of portions of the brain model as exhibiting DWMA, and determining the extent and distribution of DWMA across the model.

An impact on one or more developmental aspects of a patient may then be determined (108) based on the DWMA characteristics. This determination (108) of patient developmental impact may utilize additional information from the HIS (14), the scale impact database (18), or from other sources. For example, where the DWMA characteristics describe the size and distribution of a number of portions of the brain exhibiting DWMA, a combination of patient specific data, demographic data, and language developmental data may be used to estimate the impact that such DWMA characteristics will have on language development for the associated patient. Such impacts may be expressed in varying ways, such as a risk grouping (e.g., "high impact" or "low impact"), a color (e.g., green light indicates low risk or low impact), or a score (e.g., zero may indicate lowest risk, ten may indicate highest risk).

Patient developmental impact may also be expressed in relation to a developmental scale, evaluation, assessment, or other criteria in order to provide an objectively measurable deficit. As an example, where a set of developmental milestones provides varying ages that certain language skills are gained by, the impact may be expressed as a number of months or years that the patient's development is estimated to be delayed as compared to a standard timeline. As another example, where a developmental scale provides scores or measurements based upon evaluations at varying ages (e.g., such as the Bayley Scales of Infant and Toddler Development), the impact may be expressed as a number of points that the patient's scores will be reduced by relative to a standard subject. While patient impact may be expressed by the system (10) in varying ways, it will typically be expressed as an objectively measurable value, which is advantageous as compared to subjective analysis such as qualitative visual analysis.

An advantage of determining (108) patient impact in this manner is that the availability of an objective analysis enables the determination of an objectively measurable deficit. Medical image data associated with a particular patient will produce substantially the same results when repeatedly analyzed with steps such as those shown in FIG. 2. Similarly, medical image data associated with a plurality of patients may differ in results, but will be determined using the same objective analysis. Conversely, a subjective visual analysis of medical image data for a single patient has been shown to produce significantly different results across multiple analyses. As an example, different experts can provide different results based on the same medical image data. As another example, a single expert analyzing the same medical image data on separate days or in separate sessions can provide significantly different results for the same data. Associating a subjective analysis with a developmental scale results in a subjective indication of deficit, which may not provide a desired level of reliability, repeatability, and comparability.

The system (10) may then initiate (110) one or more impact-based treatments based on the determined (108) impact. This could include displaying or otherwise providing portions of the brain model that exhibit DWMA and/or impact datasets that describe the estimated impact on varying developmental aspects, and may also include automatically scheduling one or more tasks or other activities related to treatment. As one example, in a case where the determined (108) impact indicates a high impact on language development, the system (10) may automatically schedule a time for a developmental specialist to meet with the patient's parents soon after birth, and may also schedule a number of follow up communications, appointments, or other activities aimed to maximize treatment and intervention opportunities and effectiveness.

Figure 3:
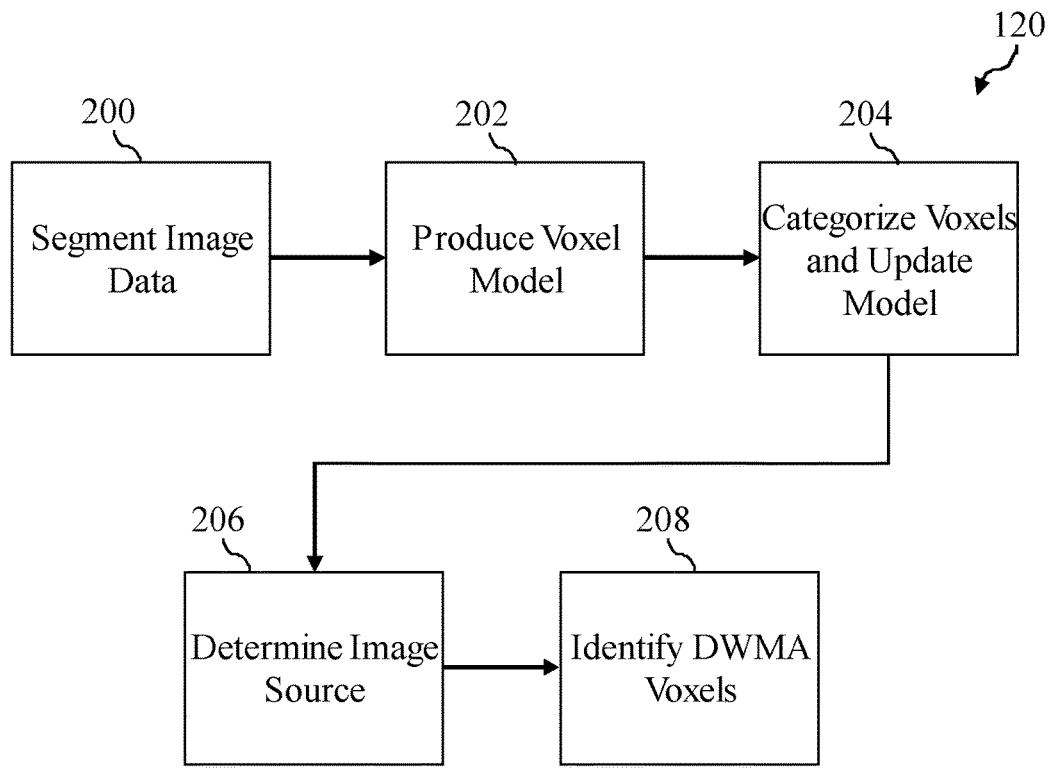
FIG. 3 is a flowchart of an exemplary set of steps that could be performed with the system of FIG. 1 to produce a brain model from medical image data.

While production of a brain model has been discussed in some detail, FIG. 3 provides further examples of steps (120) that could be performed to produce a brain model from medical image data. Once medical image data is available (e.g., such as from an MRI scan of a patient's head), the system (10) may segment (200) the image data in order to produce (202) a voxel model of the brain. Segmentation (200) may include combining multiple sets of image slices (e.g., sagittal, axial, coronal) in order to define a plurality of voxels based upon the intersections of slice. The resulting voxels are three-dimensional shapes (e.g., typically cubes) that may be individually associated with additional data that describes their spatial relationship or position within the model (e.g., adjacent slices will produce adjacent voxels) as well as attributes associated with each voxel (e.g., visual data from the image slices, signal intensity of component portions of image slices, a color or other visual representation of signal intensity). Thus, the voxel model produced (202) from segmentation is a three-dimensional representation of the combined sets of image slices built from a plurality of voxels.

The produced voxel model (202) may also be analyzed and each voxel may be categorized (204) into types associated with subsequent objective analysis of DWMA. This could include categorizing each voxel as a certain tissue type (e.g., bone, fluid, gray matter) based upon the signal intensity or other information associated with the voxel and originating from the voxel's component image slice portions.

As an example, brain tissue segmentation (200) may be achieved by unified segmentation configured for intensity inhomogeneity correction with spatial priors obtained from a neonatal probabilistic atlas. The produced (202) voxels may be labeled (204) to indicate one of three main tissue classes—white matter, gray matter, and cerebrospinal fluid.

To continue the objective analysis, the system (10) may determine (206) the image source (e.g., the type, specification, or configuration of the imaging device (20) or other source device) and then analyze the voxels model to identify (208) any voxels that exhibit DWMA based upon their type, signal intensity, or other characteristics associated with each voxel. The image source may be determined (206) based upon metadata associated with the medical image data (e.g., which may indicate creation date, source device, source device configuration, or other information), may be provided by the party or device that provides the medical image data (e.g., as part of a communication with a software API or other interface), or may be resolved by a separate query (e.g., a serial number or network identifier associated with the medical image data or the device from which it originated may be queried against a database to identify stored information describing the originating device), for example.

In some implementations, identification (208) or classification of DWMA voxels may be based in part upon the determined (206) image source information. Factors such as the manufacturer and type of the imaging device (20), as well as the scan configurations and other conditions may influence the characteristics of the resulting image slices, and may also influence the characteristics associated with voxels of the voxel model. As an example, the signal intensity (e.g., represented as grayscale colors in an image slice) that is associated with white matter, grey matter, cerebrospinal fluid, or other tissues may vary by manufacturer, or may vary depending upon configurations used during the Mill scan. Image source information may be used to account for such variances and mitigate the impact of different imaging devices (20) and scanning configurations on the results of objective analysis of DWMA.

When identifying (208) voxels as being associated with DWMA, the characteristics of those voxels may be compared to the characteristics of other voxels within the voxel model, or may be compared to stored characteristics that are associated with DWMA or healthy tissue. In some implementations, voxels may be identified (208) as exhibiting DWMA based upon their signal intensity relative to the signal intensity of voxels elsewhere in the model (e.g., adjacent voxels, or voxels elsewhere in the model that are representative of cerebral tissues). As an example, this may include identifying DWMA in voxels having a signal intensity value that exceeds the mean signal intensity value of cerebral tissues (e.g., white matter and grey matter), as measured across the voxel model, by a configured amount (e.g., 1.0 standard deviation, 2.0 standard deviation). The configured threshold may vary based upon the image source, and may be expressed in terms of standard deviation. As an example, the threshold for identifying voxels as exhibiting DWMA based upon signal intensity values may be between about 1.5 and about 2.0 standard deviations for an exemplary MRI device (e.g., a 3T Siemens Skyra MRI scanner). A standard deviation of 1.8 signal intensity above the mean of cerebral tissues provides an advantageous cut-off.

Figure 4:
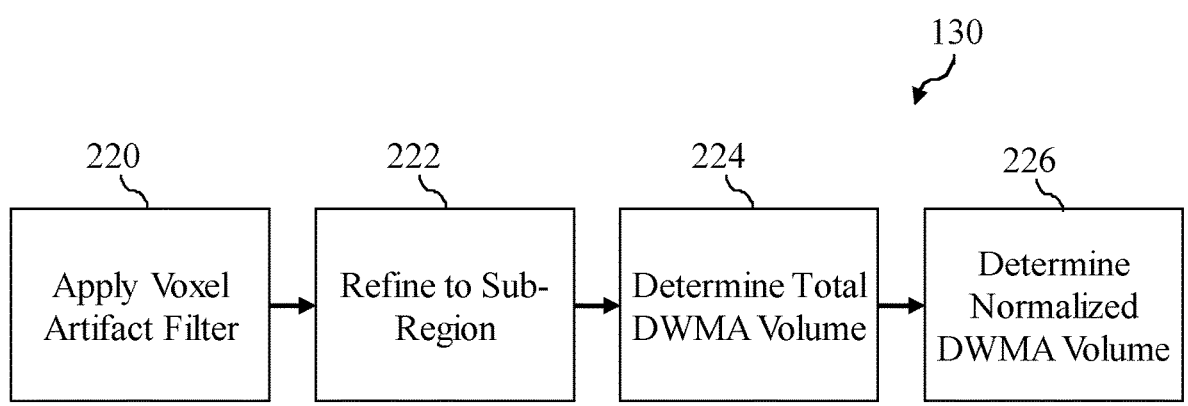
FIG. 4 is a flowchart of an exemplary set of steps that could be performed with the system of FIG. 1 to determine a set of DWMA characteristics of the brain model.

While determination of DWMA characteristics has been discussed in some detail, FIG. 4 provides further examples of steps (130) that could be performed to determine a set of DWMA characteristics of the brain model. Determining the DWMA characteristics may include applying a voxel artifact filter (220) in order to mitigate the effect of any imaging and segmentation artifacts. This may include, for example, analyzing the voxel model and/or the underlying pixels of the image slices and controlling for partial volume artifacts or partial volume voxels by reclassifying pixels or voxels that may have mixed tissue membership (e.g., a high probability of including at least >10% CSF or gray matter tissue) as non-DWMA tissue. Filtering may also include analyzing the voxel model and filtering or excluding any randomly isolated voxels that are present within the voxel model in order to mitigate any negative impact that such erroneous voxels might cause. Randomly isolated voxels may be identified based upon matching certain configured criteria (e.g., singular or small numbers of voxels that are entirely surrounded by voxels having a substantially different signal intensity, such as a single white matter voxel completely surrounded by cerebrospinal fluid, bone, or a cavity or void), and will often be caused by imaging or segmentation artifacts.

Other characteristics that may be checked for during artifact filtering (220) may include adjustments or filtering to account for low contrast to noise ratio in input image data, filtering of artifacts caused by high motion, filtering of artifacts related to high signal-to-noise ratio resulting from accelerated scan time, and filtering or correction of artifacts resulting from limited or unavailable spatial information.

Other characteristics that may be checked for during artifact filter (220) for randomly isolated voxels may include checking for voxels identified as tissue interfaces (e.g. gray-white, gray-CSF, or white-CSF) that are impacted by partial volume effects (e.g., mixture of tissue types), which can significantly impact the voxel intensity and result in false labeling as DWMA. Randomly isolated voxels may also be identified and filtered when one or a small number of voxels are present in white matter, especially subcortical white matter, since DWMA is generally regarded as a diffuse abnormality and because it is more commonly observed in the periventricular white matter as opposed to subcortical white matter.

Other techniques that may be applied during automatic artifact filtering (220) may include, in the unified segmentation model, controlling for partial volume artifacts by assuming that the intensity distribution of each class may or may not be Gaussian (e.g., a mixture of Gaussians). Gaussians may be associated with configured thresholds or ranges, that may be influenced by the determined (206) image source (e.g., in some scenarios numbers for Gaussians may be three for grey matter and two for white matter, two for cerebrospinal fluid and five for other tissue or matter). Other filtering (220) techniques may include correcting for residual partial volume artifacts by applying morphological corrections configured with criteria to verify that the outer surface of the extra-axial cerebrospinal fluid contains no brain matter, and the region in between the extra-axial cerebrospinal fluid and grey matter contains no white matter.

simple but effective knowledge-based morphological corrections are further conducted. The correction criteria are that the outer surface of extra-axial CSF contains no brain matters and the region in between extra-axial CSF and GM contains no WM.

In addition for the partial volume correction, in the unified segmentation model, the intensity inhomogeneity correction was also included in the mixture of Gaussian by extra parameters that account for smooth intensity variations.

Determining DWMA characteristics may also include refining (222) the voxel model to include only certain sub-regions of the brain. As has been described, the development and verification of the disclosed system and process for objective analysis of DWMA indicates that the centrum semiovale region is a common location for the occurrence of DWMA. An emphasis on the centrum semiovale is also advantageous because that region of the brain is not confounded by the normal occurrence of high signal intensity as seen in periventricular developmental crossroads regions, which can adversely impact diagnostic reliability. For these reasons and others, objective analysis of DWMA from the centrum semiovale region provides better predictive output than analysis of the entire brain. In some implementations, the voxel model may be refined (222) to the centrum semiovale region in order to take advantage of such improvements.

After performing any preparatory steps (e.g., identification (208) of DWMA voxels, filtering (220), refining (222), the voxel model may be analyzed to determine (224) a total DWMA volume based on the number of DWMA exhibiting voxels. As an example, total volume of DWMA may be calculated (224) as the product of voxel volume (e.g., the configured scale or resolution of voxels) and total number of DWMA voxels present in DWMA regions of the voxel model. The system (10) may then determine (226) a normalized DWMA volume based upon the total DWMA volume and the total white matter volume of the voxel model. As an example, normalized DWMA volume may be calculated (226) as the quotient of total DWMA volume divided by total white matter volume of the voxel model. Determined DWMA characteristic, such as the total DWMA volume, normalized DWMA volume, white matter volume, grey matter volume, and other characteristics associated with the voxel model may be stored and used when determining (108) the patient impact. As should be apparent, these determined DWMA characteristics are objective values, and so can provide reliable comparable values across a plurality of analyses as compared to subjective visual analysis or other qualitative assessments.

Figure 5:
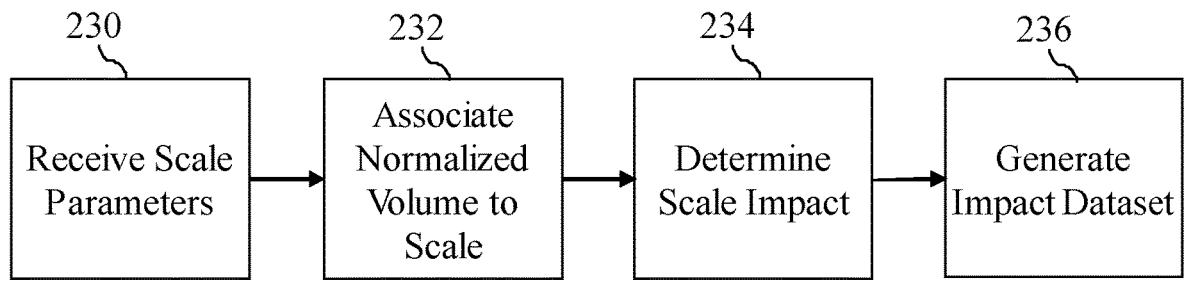
FIG. 5 is a flowchart of an exemplary set of steps that could be performed with the system of FIG. 1 to determine an impact estimate for the brain model.

With the availability of such objective values and a reliable association between DWMA characteristics and child development it is possible to objectively determine developmental impacts on patients instead of relying upon subjective non-standard evaluations. While determination of patient impact has been discussed in some detail, FIG. 5 provides further examples of steps (140) that could be performed to determine an impact estimate for the brain model. The system (10) may receive (230) a set of scale parameters from the scale impact database (18) or another source, and may associate (232) one or more of the DWMA characteristics to the scale parameters.

The scale parameters may define one or more developmental scales, evaluations, or other assessments, and may also include data that describes the relationship between DWMA characteristics (e.g., normalized DWMA volume, objectively analyzed severe DWMA) and the one or more developmental scales. This relationship may be expressed based upon static criteria or dynamic datasets (e.g., the system (10) may be configured to automatically update the scale impact database (18) based upon subsequent treatment, intervention, and evaluation steps), may be expressed as linear or non-linear relationships between DWMA volume or grade and particular developmental scores, may be expressed as certain ranges of impact (e.g., normalized DWMA volume of 5-10% indicates a developmental deficiency of 10-15 points, 11-15% indicates a deficiency of 15-25 points, etc.), or may be expressed in other ways as will be apparent to those of ordinary skill in the art in light of this disclosure.

The set of DWMA characteristics and associated scale parameters may then be used to determine (234) the development impact of objectively analyzed DWMA for a particular patient as has been described, and may be used to generate (236) an impact dataset based thereon. The impact dataset may include, for example, viewable portions of some or all of the voxel model, some or all of the image slices from the medical image data, modified portions of the voxel model that include visually distinctive markings for voxels or regions that indicate objectively identified DWMA, and information describing one or more determined (234) scale impacts. The information describing scale impacts may include, for example, descriptions of a developmental scale that is associated with DWMA characteristics (e.g., a cognitive, language, motor, or other developmental scale such as the Bayley-III) and a description of that association (e.g., an indication of the extent and magnitude to which particular DWMA characteristics are likely to affect each particular developmental scale). The generated (236) impact dataset may be saved, provided to other devices, or otherwise used to initiate impact-based treatment (110) or perform other post-analysis actions.

Figure 6:
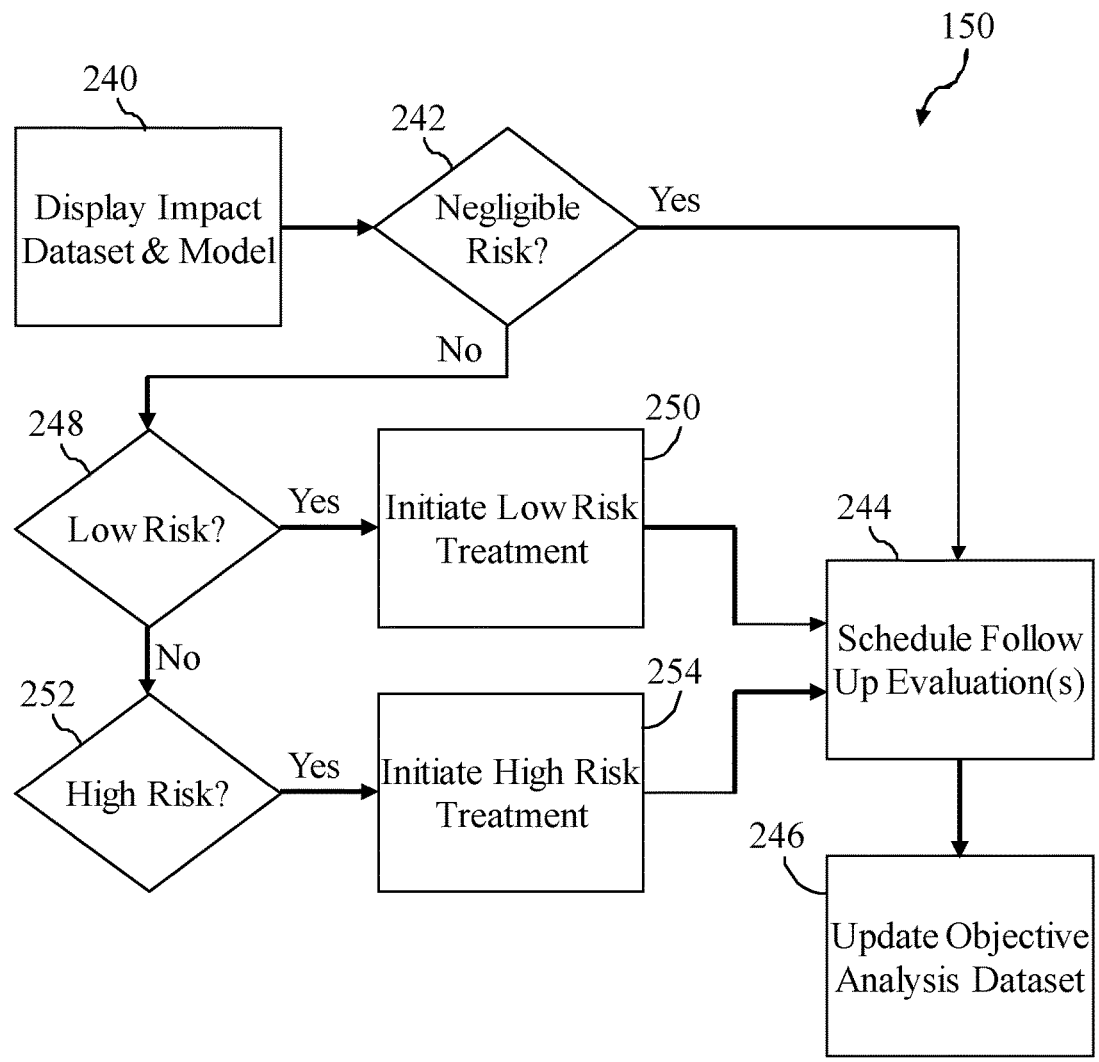
FIG. 6 is a flowchart of an exemplary set of steps that could be performed with the system of FIG. 1 to provide information and initiate treatment for an impact estimate.

While post impact analysis actions have been discussed in some detail, FIG. 6 further examples of steps (150) that could be performed to provide information and initiate treatment based on impact estimates. These steps may include displaying (240) some or all of the impact dataset as text or numerical data, graphs, charts, or other data structures, and may also include displaying image data associated with the voxel model or image slices. Images may be displayed via a display or user interface of the imaging device (20), may be displayed on a device accessing records or interfaces on the HIS (14), or may be transmitted to one or more user devices (16) that are associated with employees or service providers.

As an example of image data that may be displayed, FIGS. 7A-7C show medical image data that may be displayed during objective analysis of DWMA. FIG. 7A shows an image slice (300) that depicts a portion of a brain (e.g., the centrum semiovale) as may be produced by an MRI scanner during capture (102). FIG. 7B shows an image slice (302) that has been modified during objective analysis to visually identify DWMA within the depicted portion. FIG. 7C shows a section (304) of the image slice (302) that includes several highlighted portions of DWMA. As a result of objective analysis, a first portion (306*a*) of DWMA has been identified and marked on the right side of the section (304), while a second portion (306*b*) of DWMA has been identified and marked on the right side of the section (304). Displayed image data may be useful in supporting or explaining an objective analysis of DWMA, and may also provide a useful comparison to subjective visual diagnosis of DWMA for the same or similar patients.

Post-analysis steps may also include automatically assessing the objectively determined developmental impacts and categorizing each infant into varying treatment or intervention groups based thereon. As an example, some pre-term infants may exhibit little objective evidence of DWMA and may be assigned to a negligible risk category (242). Where there is negligible risk, the system (10) may not initiate any immediate actions, but may schedule one or more follow up evaluations (244). Scheduled (244) tasks may include automated data collection steps to query the HIS (14) or other systems upon regular intervals for information associated with the infant, which may be used to verify the results of objective analysis (e.g., where no developmental deficits are observed at subsequent ages), or may be used to update or improve the accuracy and effectiveness of objective analysis dataset (246) and process. As an example, where scheduled (244) tasks gather data indicating inaccuracies in the objective analysis results, such data may be used to refine the configured steps and parameters for identifying (208) DWMA voxels, filtering artifacts (220), refining voxel models (222), determining (224) DWMA volume, determining (226) normalized DWMA volume, determining scale impact (234), or categorizing patients into risk categories.

Such scheduled task (244) may also include automatically triggering communications and/or creating appointments to enable manual evaluation and follow up for patients at various ages. During such manual follow ups, the user device (16) may be configured to provide a software application or software interface that is customized to provide questions, tasks, and other information related to a follow up evaluation, and to receive information, responses, and other inputs during manual follow. Software applications that aid in manual follow up may automatically format such data and provide it to the HIS (14) and/or the image processor (12) where it can be used to improve and refine the objective analysis process, as has been described.

Where an infant is assigned to a low-risk category (248), the system (10) may initiate (250) one or more treatment actions related to intervention and treatment for low/moderate developmental deficits. This may include automated communications with care providers (e.g., notifying a user device (16) associated with a developmental counselor to contact the patient's guardian), automated scheduling of services, automated compilation and delivery of various informational resources related to developmental deficits, and other similar tasks. A low risk categorization (248) may also include scheduling (244) of follow up evaluation and data collection for updating (246) and improving the objective analysis dataset, as has been described.

Where an infant is assigned to a high-risk category (252), the system (10) may initiate (254) one or more treatment actions related to intervention and treatment for moderate/high development deficits. This may include automated steps similar to those initiated for low risk treatment (250), but may include additional steps such as initiating more aggressive interventional treatment, providing information on experimental treatment trials that may be available, or other treatment steps appropriate for developmental risks of a higher magnitude. Automatically Scheduled (244) follow up tasks and actions may also be of a different type or higher frequency as compared to other scheduled (244) tasks, and information provided during follow up may similarly be used to update (246) the objective analysis dataset, as has been described.

Figure 8:
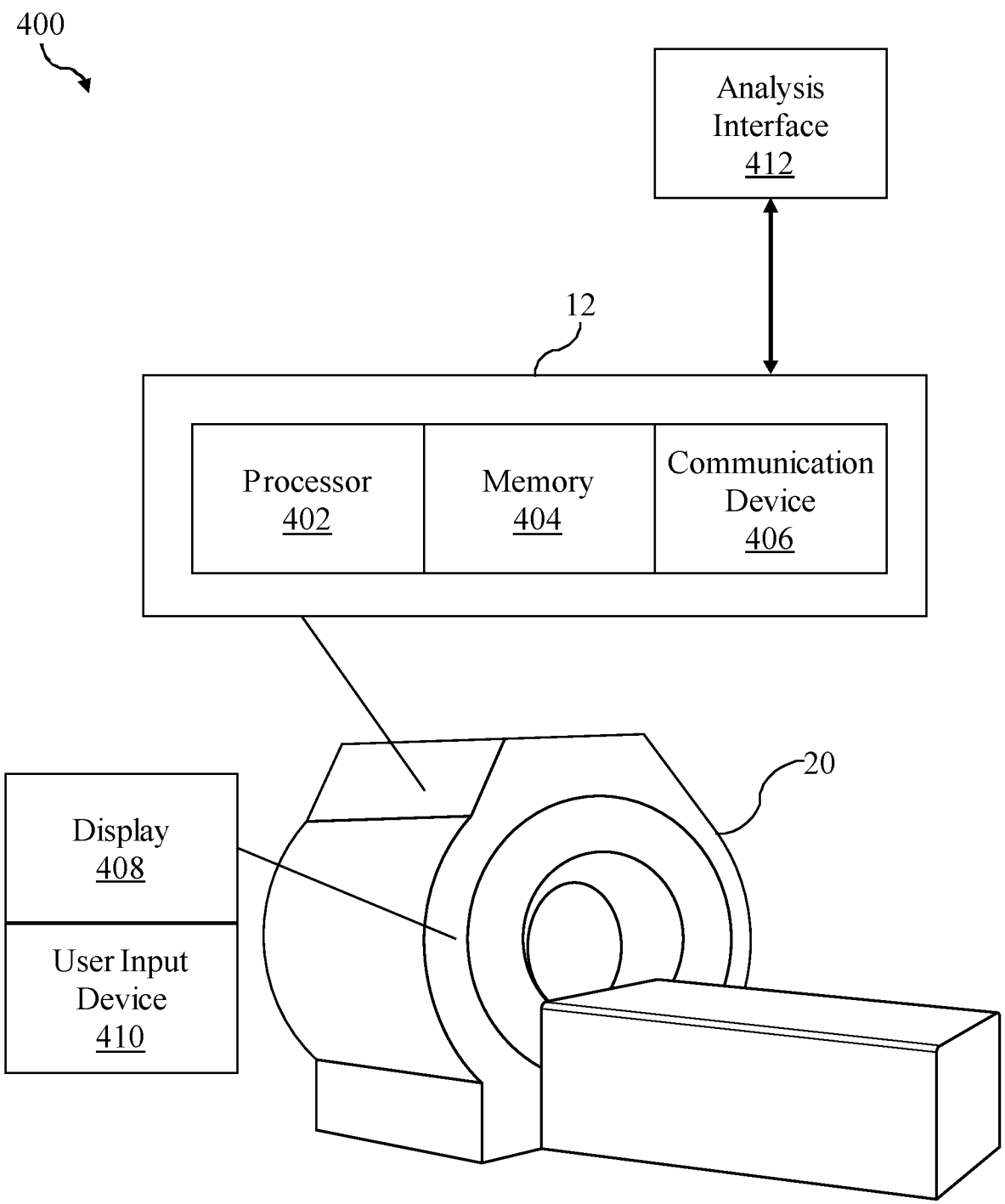
FIG. 8 is a schematic diagram of an alternate exemplary system configured to perform objective analysis of medical image data for white matter abnormalities.

While various features and embodiments of the system (10) have been discussed, other variations and examples exist and will be apparent to those of ordinary skill in the art in light of the disclosure herein. As an example, FIG. 8 is a schematic diagram of an alternate exemplary system (400) configured to perform objective analysis of medical image data for white matter abnormalities. In FIG. 8, the imaging device (20) is an Mill machine or other medical image capture equipment such as may be present and used in neonatal settings. The Mill machine includes a display (408) and user input device (410) usable by a care provider to interact with the machine to configure settings, perform scanning, or display output. The display (408) and user input device (410) may be located on the MM machine itself or may be located in a separate room as an external or peripheral component of the MRI machine. The MRI machine also includes the image processor (12) (e.g., as components within the MM machine itself, or located in a sperate room as external or peripheral components), which itself includes a processor (402), a memory (404), and a communication device (406) (e.g., a wireless or wired communication device allowing the image processor (12) to communicate with other devices, networks, or systems).

In such an implementation, the image processor (12) may be configured to perform the objective analysis in parallel (e.g., as medical image data is captured) or in sequence (e.g., after all capture is complete) with conventional medical imaging of an infant with the imaging device (20). Results of the objective analysis may be provided via the display (408) in parallel with ongoing imaging (e.g., such as where analysis may be performed immediately after completion of imaging for the centrum semiovale region, since other unscanned portions are not relied upon), or may be provided soon after imaging is completed. This advantageously allows for objective analysis to be performed in parallel with pre-existing procedures, instead of requiring additional manual steps and/or reliance on separate equipment. This also advantageously allows for the results of objective analysis to be rapidly available at the point of care, and may allow for more immediate responses with automated and manual intervention and treatment. For example, in some cases the results of objective analysis may prompt additional scanning (e.g., to verify results, or to rescan with a different focus or resolution), which could be performed immediately and during the same session while the infant is still present and prepared for scanning.

In some implementations of the system (400), the image processor (12) may be in communication with an analysis interface (412) via the communication device (406) or another network device. The image processor (12) may perform some steps, such as capturing (102) of image data and some or all of the steps of production (104) of the brain model, and may transmit the results of such processing to a remote server for further analysis via the analysis interface (412). The analysis interface (412) may be an API or other software interface or channel configured to receive medical image data as input, and to generate (236) and provide an impact dataset to be returned to the image processor (12) or the HIS (14) as output. Such an implementation may be advantageous because the bulk of processing during objective analysis may be performed by an external or third-party device such as a cloud computing environment, which will reduce the impact on the care providers systems and networks (e.g., the imaging device (20), image processor (12), and HIS (14)). This may allow for objective analysis of DWMA to be retrofitted into a wide variety of pre-existing imaging devices and other equipment without costly requirements in hardware upgrades or complex software configurations.

III. Objective Analysis of DWMA for Motor Function

As has been described, the disclosed system (10) for objective analysis of DWMA for impact on cognitive and language development may also be configured to provide analysis for other aspects of infant development such as motor development. Development and verification of the system (10) included examining the relationship between DWMA characteristics (e.g., such as normalized volume of DWMA) and Bayley-III motor scores at 2 years corrected age using linear regression. This included evaluating the independent prognostic value of normalized volume of DWMA by performing multivariable regression models and adding known perinatal predictors of Bayley score, including sex, gestational age, and global brain abnormality scores, as well as controlling for the location and PMA of infants as has been described.

Secondary analysis included logistic regression adjusted for global brain abnormality score assessed the odds of development of cerebral palsy and motor impairment for infants with objectively analyzed severe DWMA. Predictions were assessed using Fisher's exact test to evaluate the prognostic properties of objectively analyzed severe DWMA, moderate injury on structural MM, and visually diagnosed severe DWMA.

Preterm infants with severe brain injury and excessive motion artifacts were excluded from the assessment. Bayley-III mean motor score at 24 months corrected age was 95.8. Motor impairment using a Bayley threshold of <85 was diagnosed in 21.7% of infants. Cerebral palsy was diagnosed in 7.3% of infants. Other conditions diagnosed in small numbers were spastic diplegia, ataxic cerebral palsy, spastic left hemiplegia, and spastic quadriplegia.

Structural MRI was performed at a mean PMA of 40.4 weeks for cerebral palsy diagnosis. Based on the global brain abnormality score, 13.4% of infants were classified with moderate injury, 31.7% were classified with mild injury, and 54.9% were classified with no injury. Structural MRI was abnormal in 50% of infants diagnosed with cerebral palsy. Visual subjective analysis of DWMA diagnosed 13.4% of infants as severe, 26.8% as moderate, and 59.8% as mild or no DWMA.

Objective analysis of DWMA at varying thresholds (e.g., between about 1.0 and about 2.0 standard deviations) of signal intensity were significantly correlated with Bayley motor score, while a threshold of 1.8 standard deviations exhibited a highest prediction accuracy, though such thresholds may vary based on the image source and scanning configurations, as has been described. This association remained significant for normalized DWMA volume and raw DWMA volume. In multivariable analysis, controlling for other known predictors of Bayley scores, normalized volume of DWMA remained a significant predictor motor development at 2 years corrected age. A 10% increase in objectively analyzed DWMA volume at term was predictive of a 19.4-point reduction in Bayley III motor scores at 2 years corrected age. Conversely, visual qualitative diagnosis of DWMA was not significantly predictive of motor scores.

As will be apparent from the above example, objectively analyzed DWMA provides a useful predictor for the development of motor function. The system (10) may be configured to objectively analyze DWMA and motor function as has already been described in FIGS. 2-6 and elsewhere, and varying implementations of the system (10) may be configured to determine developmental impacts on one or more of motor function, cognitive function, language, or other aspects of development that objectively analyzed DMWA is predictive of.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for objectively analyzing medical image data for diffuse white matter abnormality (DWMA), the system comprising a display and a processor configured to: (i) receive a set of image data that is associated with a brain of a patient and produce a voxel model based on the set of image data, wherein the voxel model comprises a plurality of voxels, wherein each voxel in the plurality of voxels is associated with a set of voxel attributes, (ii) associate each voxel within the plurality of voxels with a white matter attribute, a grey matter attribute, or a cerebrospinal fluid attribute based on the sets of voxel attributes, (iii) identify a set of DWMA voxels within the plurality of voxels based on the set of voxel attributes, (iv) determine a set of DWMA characteristics based on the set of DWMA voxels and the plurality of voxels, (v) determine a patient developmental impact based on the set of DWMA characteristics, and (vi) display the patient developmental impact via the display.

Example 2

The system of example 1, wherein the processor is further configured to, when determining the set of DWMA characteristics, determine a total DWMA volume based on the set of DWMA voxels and a voxel volume attribute associated with the voxel model.

Example 3

The system of example 2, wherein the processor is further configured to: (i) determine a total volume of voxels associated with the white matter attribute in the voxel model based on the plurality of voxels and the voxel volume attribute, and (ii) determine a normalized DWMA volume based on the total DWMA volume and the total volume of voxels associated with the white matter attribute.

Example 4

The system of any one or more of examples 1 through 3, wherein the processor is further configured to: (i) identify any partial volume voxels within the plurality of voxels and associate the partial volume voxels with a cerebral tissue attribute, and (ii) identify any randomly isolated voxels within the plurality of voxels based on a set of adjacent voxels, and remove the randomly isolated voxels from the plurality of voxels.

Example 5

The system of any one or more of examples 1 through 4, wherein the processor is further configured to: (i) identify a centrum semiovale region within the voxel model, and (ii) remove any voxels from the plurality of voxels that are not within the centrum semiovale region.

Example 6

The system of any one or more of examples 1 through 5, wherein the processor is further configured to, when identifying the set of DWMA voxels: (i) determine a signal intensity attribute associated with each voxel within the plurality of voxels, wherein the signal intensity attribute is based on the signal intensity of the medical image data, (ii) identify a set of cerebral tissue voxels within the plurality of voxels, wherein the set of cerebral tissue voxels comprises each voxel from the plurality of voxels that is associated with the white matter attribute or the grey matter attribute, (iii) determine a mean signal intensity for the set of cerebral tissue voxels based on their signal intensity attributes, and (iv) identify the set of DWMA voxels based on their signal intensity attributes exceeding a configured threshold above the mean signal intensity.

Example 7

The system of any one or more of examples 1 through 6, wherein the processor is further configured to: (i) determine an image source from which the set of image data originated, and (ii) determine the configured threshold for signal intensity based upon the image source, wherein the configured threshold is a standard deviation between about 1.0 and about 2.0.

Example 8

The system of any one or more of examples 1 through 7, wherein the processor is further configured to, when producing the voxel model: (i) receive a set of preconfigured spatial priors, wherein the set of preconfigured spatial priors are associated with a neonatal probabilistic atlas, and (ii) perform a unified segmentation of the set of image data with intensity inhomogeneity correction and the preconfigured spatial priors.

Example 9

The system of any one or more of examples 1 through 8, wherein the processor is further configured to, when determining the patient developmental impact: (i) receive a set of developmental scale parameters that describe one or more developmental scales usable to evaluate at least one aspect of infant development, (ii) determine a relationship between the set of DWMA characteristics and the set of developmental scale parameters, and (iii) determine a score deficit for the one or more developmental scales based on the relationship.

Example 10

The system of example 9, wherein the one or more developmental scales comprise: (i) a first scale describing cognitive development, (ii) a second scale describing motor function development, and (iii) a third scale describing language development.

Example 11

The system of any one or more of examples 9 through 10, wherein the one or more developmental scales comprise the Bayley Scales of Infant and Toddler Development.

Example 12

The system of any one or more of examples 1 through 11, wherein the patient developmental impact describes an objectively measurable deficit in at least one aspect of the patient's development.

Example 13

The system of example 12, wherein the processor is further configured to, when displaying the patient developmental impact: (i) display a modified voxel model, wherein the modified voxel model comprises the plurality of voxels and a plurality of indicators that visually identify the set of DWMA voxels within the plurality of voxels, (ii) display the objectively measurable deficit as a score deficit for at least one infant development scale, and (iii) display a description of the infant development scale.

Example 14

The system of any one or more of examples 1 through 13, wherein the processor is further configured to: (i) determine whether the patient developmental impact is above an objective threshold indicating a high deficit, and (ii) initiate a treatment plan for the patient when the patient developmental impact is above the objective threshold.

Example 15

A method for objectively analyzing medical image data for diffuse white matter abnormality (DWMA) comprising: (i) at an image processor, receiving a set of image data that is associated with a brain of a patient and producing a voxel model based on the set of image data, wherein the voxel model comprises a plurality of voxels, wherein each voxel in the plurality of voxels is associated with a set of voxel attributes, (ii) associating each voxel in the plurality of voxels with a white matter attribute, a grey matter attribute, or a cerebrospinal fluid attribute based on the sets of voxel attributes, (iii) identifying a set of DWMA voxels within the plurality of voxels based on the set of voxel attributes, (iv) determining a set of DWMA characteristics based on the set of DWMA voxels and the plurality of voxels, (v) determining a patient developmental impact based on the set of DWMA characteristics, wherein the patient developmental impact describes an objectively measurable deficit in at least one aspect of the patient's development, and (vi) causing a display to display the patient developmental impact.

Example 16

The method of example 15, further comprising, when determining the set of DWMA characteristics, determining a total DWMA volume based on the set of DWMA voxels and a voxel volume attribute associated with the voxel model.

Example 17

The method of example 16, further comprising: (i) determining a total volume of voxels associated with the white matter attribute in the voxel model based on the plurality of voxels and the voxel volume attribute, and (ii) determining a normalized DWMA volume based on the total DWMA volume and the total volume of voxels associated with the white matter attribute.

Example 18

The method of any one or more of examples 15 through 17, further comprising, when identifying the set of DWMA voxels: (i) determining a signal intensity attribute associated with each voxel within the plurality of voxels, wherein the signal intensity attribute is based on the signal intensity of the medical image data, (ii) identifying a set of cerebral tissue voxels within the plurality of voxels, wherein the set of cerebral tissue voxels comprises each voxel from the plurality of voxels that is associated with the white matter attribute or the grey matter attribute, (iii) determining a mean signal intensity for the set of cerebral tissue voxels based on their signal intensity attributes, and (iv) identifying the set of DWMA voxels based on their signal intensity attributes exceeding a configured threshold above the mean signal intensity.

Example 19

A magnetic resonance imaging (MRI) platform operable to capture a set of image data of a brain of a patient, comprising: (a) an MRI scanner; (b) a processor; (c) a display positioned proximately to a point of care associated with the MRI scanner; wherein the processor is configured to: (i) produce a voxel model based on the set of image data, wherein the voxel model comprises a plurality of voxels, wherein each voxel in the plurality of voxels is associated with a set of voxel attributes, (ii) associate each voxel within the plurality of voxels with a white matter attribute, a grey matter attribute, or a cerebrospinal fluid attribute based on the sets of voxel attributes, (iii) identify a set of DWMA voxels within the plurality of voxels based on the set of voxel attributes, (iv) determine a set of DWMA characteristics based on the set of DWMA voxels and the plurality of voxels, (v) determine a patient developmental impact based on the set of DWMA characteristics, wherein the patient developmental impact describes an objectively measurable deficit in at least one aspect of the patient's development, and (vi) display the patient developmental impact via the display at the point of care.

Example 20

The Mill platform of example 19, wherein the processor is further configured to: (i) automatically determine and display the patient developmental impact when the set of image data is captured by the MM scanner, and (ii) when determining the patient developmental impact: (A) receive a set of developmental scale parameters that describe one or more developmental scales usable to evaluate at least one aspect of infant development, (B) determine a relationship between the set of DWMA characteristics and the set of developmental scale parameters, and (C) determine a score deficit for the one or more developmental scales based on the relationship.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A system for objectively analyzing medical image data for diffuse white matter abnormality (DWMA), the system comprising a display and a processor configured to:
   (i) receive a set of image data that is associated with a brain of a patient and produce a voxel model based on the set of image data, wherein the voxel model comprises a plurality of voxels, wherein each voxel in the plurality of voxels is associated with a set of voxel attributes,
   (ii) associate each voxel within the plurality of voxels with a white matter attribute, a grey matter attribute, or a cerebrospinal fluid attribute based on the sets of voxel attributes,
   (iii) identify a set of DWMA voxels within the plurality of voxels based on the set of voxel attributes,
   (iv) determine a set of DWMA characteristics based on the set of DWMA voxels and the plurality of voxels,
   (v) determine a patient developmental impact based on the set of DWMA characteristics, and
   (vi) display the patient developmental impact via the display,
   (vii) determine a total DWMA volume based on the set of DWMA voxels and a voxel volume attribute associated with the voxel mode when determining the set of DWMA characteristics,
   (viii) determine a total volume of voxels associated with the white matter attribute in the voxel model based on the plurality of voxels and the voxel volume attribute, and
   (ix) determine a normalized DWMA volume based on the total DWMA volume and the total volume of voxels associated with the white matter attribute.

2. The system of claim 1, wherein the processor is further configured to:
   (i) identify any partial volume voxels within the plurality of voxels and associate the partial volume voxels with a cerebral tissue attribute, and
   (ii) identify any randomly isolated voxels within the plurality of voxels based on a set of adjacent voxels, and remove the randomly isolated voxels from the plurality of voxels.

3. The system of claim 1, wherein the processor is further configured to:
   (i) identify a centrum semiovale region within the voxel model, and
   (ii) remove any voxels from the plurality of voxels that are not within the centrum semiovale region.

4. The system of claim 1, wherein the processor is further configured to, when identifying the set of DWMA voxels:
   (i) determine a signal intensity attribute associated with each voxel within the plurality of voxels, wherein the signal intensity attribute is based on the signal intensity of the medical image data,
   (ii) identify a set of cerebral tissue voxels within the plurality of voxels, wherein the set of cerebral tissue voxels comprises each voxel from the plurality of voxels that is associated with the white matter attribute or the grey matter attribute,
   (iii) determine a mean signal intensity for the set of cerebral tissue voxels based on their signal intensity attributes, and
   (iv) identify the set of DWMA voxels based on their signal intensity attributes exceeding a configured threshold above the mean signal intensity.

5. The system of claim 4, wherein the processor is further configured to:
   (i) determine an image source from which the set of image data originated, and
   (ii) determine the configured threshold for signal intensity based upon the image source,
   wherein the configured threshold is a standard deviation between 1.0 and about 2.0.

6. The system of claim 1, wherein the processor is further configured to, when producing the voxel model:
   (i) receive a set of preconfigured spatial priors, wherein the set of preconfigured spatial priors are associated with a neonatal probabilistic atlas, and
   (ii) perform a unified segmentation of the set of image data with intensity inhomogeneity correction and the preconfigured spatial priors.

7. The system of claim 1, wherein the processor is further configured to, when determining the patient developmental impact:
   (i) receive a set of developmental scale parameters that describe one or more developmental scales usable to evaluate at least one aspect of infant development,
   (ii) determine a relationship between the set of DWMA characteristics and the set of developmental scale parameters, and
   (iii) determine a score deficit for the one or more developmental scales based on the relationship.

8. The system of claim 7, wherein the one or more developmental scales comprise:
   (i) a first scale describing cognitive development,
   (ii) a second scale describing motor function development, and
   (iii) a third scale describing language development.

9. The system of claim 7, wherein the one or more developmental scales comprise the Bayley Scales of Infant and Toddler Development.

10. The system of claim 1, wherein the patient developmental impact describes an objectively measurable deficit in at least one aspect of the patient's development.

11. The system of claim 10, wherein the processor is further configured to, when displaying the patient developmental impact:
(i) display a modified voxel model, wherein the modified voxel model comprises the plurality of voxels and a plurality of indicators that visually identify the set of DWMA voxels within the plurality of voxels,
(ii) display the objectively measurable deficit as a score deficit for at least one infant development scale, and
(iii) display a description of the infant development scale.

12. A system for objectively analyzing medical image data for diffuse white matter abnormality (DWMA), the system comprising a display and a processor configured to:
(i) receive a set of image data that is associated with a brain of a patient and produce a voxel model based on the set of image data, wherein the voxel model comprises a plurality of voxels, wherein each voxel in the plurality of voxels is associated with a set of voxel attributes,
(ii) associate each voxel within the plurality of voxels with a white matter attribute, a grey matter attribute, or a cerebrospinal fluid attribute based on the sets of voxel attributes,
(iii) identify a set of DWMA voxels within the plurality of voxels based on the set of voxel attributes,
(iv) determine a set of DWMA characteristics based on the set of DWMA voxels and the plurality of voxels,
(v) determine a patient developmental impact based on the set of DWMA characteristics, and
(vi) display the patient developmental impact via the display,
(vii) determine whether the patient developmental impact is above an objective threshold indicating a high deficit, and
(viii) initiate a treatment plan for the patient when the patient developmental impact is above the objective threshold.

13. A method for objectively analyzing medical image data for diffuse white matter abnormality (DWMA) comprising:
(i) at an image processor, receiving a set of image data that is associated with a brain of a patient and producing a voxel model based on the set of image data, wherein the voxel model comprises a plurality of voxels, wherein each voxel in the plurality of voxels is associated with a set of voxel attributes,
(ii) associating each voxel in the plurality of voxels with a white matter attribute, a grey matter attribute, or a cerebrospinal fluid attribute based on the sets of voxel attributes,
(iii) identifying a set of DWMA voxels within the plurality of voxels based on the set of voxel attributes,
(iv) determining a set of DWMA characteristics based on the set of DWMA voxels and the plurality of voxels,
(v) determining a patient developmental impact based on the set of DWMA characteristics, wherein the patient developmental impact describes an objectively measurable deficit in at least one aspect of the patient's development, and
(vi) causing a display to display the patient developmental impact,
(vii) determining a total DWMA volume based on the set of DWMA voxels and a voxel volume attribute associated with the voxel model when determining the set of DWMA characteristics,
(viii) determining a total volume of voxels associated with the white matter attribute in the voxel model based on the plurality of voxels and the voxel volume attribute, and
(ix) determining a normalized DWMA volume based on the total DWMA volume and the total volume of voxels associated with the white matter attribute.

14. The method of claim 13, further comprising, when identifying the set of DWMA voxels:
(i) determining a signal intensity attribute associated with each voxel within the plurality of voxels, wherein the signal intensity attribute is based on the signal intensity of the medical image data,
(ii) identifying a set of cerebral tissue voxels within the plurality of voxels, wherein the set of cerebral tissue voxels comprises each voxel from the plurality of voxels that is associated with the white matter attribute or the grey matter attribute,
(iii) determining a mean signal intensity for the set of cerebral tissue voxels based on their signal intensity attributes, and
(iv) identifying the set of DWMA voxels based on their signal intensity attributes exceeding a configured threshold above the mean signal intensity.

\* \* \* \* \*